(12) United States Patent
Nishimoto et al.

(10) Patent No.: US 10,458,956 B2
(45) Date of Patent: Oct. 29, 2019

(54) ULTRASONIC PROBE AND ULTRASONIC DIAGNOSIS DEVICE PROVIDED WITH SAME

(71) Applicant: HITACHI, LTD., Tokyo (JP)

(72) Inventors: Takuma Nishimoto, Tokyo (JP); Yutaka Igarashi, Tokyo (JP); Yusaku Katsube, Tokyo (JP)

(73) Assignee: HITACHI, LTD., Tokyo (JP)

( * ) Notice: Subject to any disclaimer, the term of this patent is extended or adjusted under 35 U.S.C. 154(b) by 230 days.

(21) Appl. No.: 15/540,802

(22) PCT Filed: Nov. 27, 2015

(86) PCT No.: PCT/JP2015/083362
§ 371 (c)(1),
(2) Date: Jun. 29, 2017

(87) PCT Pub. No.: WO2016/114018
PCT Pub. Date: Jul. 21, 2016

(65) Prior Publication Data
US 2017/0370886 A1    Dec. 28, 2017

(30) Foreign Application Priority Data

Jan. 14, 2015   (JP) .................................. 2015-004624

(51) Int. Cl.
*G01N 29/24* (2006.01)
*G01N 29/30* (2006.01)
(Continued)

(52) U.S. Cl.
CPC ........... *G01N 29/24* (2013.01); *B06B 1/0207* (2013.01); *G01N 29/30* (2013.01); *G01N 29/32* (2013.01);
(Continued)

(58) Field of Classification Search
CPC ........ G01N 29/24; G01N 29/30; G01N 29/32; G01N 2291/106; B06B 1/0207;
(Continued)

(56) References Cited

U.S. PATENT DOCUMENTS 6,320,407 B1    11/2001   Sakamoto
2003/0151417 A1*   8/2003   Koen .................. H03G 1/0052
                                                        324/673

(Continued)

FOREIGN PATENT DOCUMENTS

CN      102883664 A    1/2013
JP      2001-119277 A  4/2001

(Continued)

OTHER PUBLICATIONS

International Search Report, dated Feb. 23, 2016, which issued during the prosecution of International Application No. PCT/JP2015/083362, which corresponds to the present application.

(Continued)

*Primary Examiner* — Daniel S Larkin
*Assistant Examiner* — Anthony W Megna Fuentes
(74) *Attorney, Agent, or Firm* — Baker Botts L.L.P.

(57) ABSTRACT

Provided is an ultrasonic probe having an adjustable slew rate, the ultrasonic probe having minimal dimensions and circuit sizes. The ultrasonic probe includes: a transducer; a transmitting circuit; a correcting unit; and a distributing unit. The transmitting circuit includes a transducer driving unit and a current source. The transducer driving unit includes a current mirror of a low voltage transistor and a high voltage transistor. The high voltage transistor is connected to the transducer and the current source supplies an operating current to the low voltage transistor of the transducer driving unit. The correcting unit includes a transmission circuit driving unit replica, a bias unit, and an observing unit. The (Continued)

distributing unit transfers a signal to a current source of the transmitting circuit so that the same current value as the current value extracted by the observing unit flows.

10 Claims, 9 Drawing Sheets

(51) Int. Cl.
    *G01N 29/32*     (2006.01)
    *B06B 1/02*     (2006.01)
    *A61B 8/08*     (2006.01)
    *A61B 8/00*     (2006.01)

(52) U.S. Cl.
    CPC .......... *A61B 8/4405* (2013.01); *A61B 8/4455* (2013.01); *A61B 8/4477* (2013.01); *A61B 8/5269* (2013.01); *G01N 2291/106* (2013.01)

(58) Field of Classification Search
    CPC ... A61B 8/5269; A61B 8/4477; A61B 8/4455; A61B 8/4405
    See application file for complete search history.

(56) References Cited

U.S. PATENT DOCUMENTS

| | | | | |
|---|---|---|---|---|
| 2007/0085607 | A1* | 4/2007 | El Waffaoui | H03F 1/26 330/257 |
| 2008/0068105 | A1* | 3/2008 | Yajima | H03B 5/326 331/116 R |
| 2008/0200809 | A1* | 8/2008 | Shifrin | G01S 15/102 600/447 |
| 2009/0279719 | A1* | 11/2009 | Lesso | B06B 1/0292 381/174 |
| 2010/0123520 | A1* | 5/2010 | Shifrin | H03F 3/45183 330/254 |
| 2012/0014541 | A1* | 1/2012 | Nakayama | H03F 1/52 381/111 |
| 2012/0092954 | A1* | 4/2012 | Suzuki | G01S 7/52017 367/7 |
| 2012/0249210 | A1 | 10/2012 | Shimizu et al. | |
| 2012/0271172 | A1 | 10/2012 | Komuro | |
| 2013/0104658 | A1* | 5/2013 | Amemiya | G01N 29/34 73/606 |
| 2015/0318829 | A1* | 11/2015 | Astgimath | H03F 3/505 381/120 |

FOREIGN PATENT DOCUMENTS

| | | |
|---|---|---|
| JP | 2012-019015 A | 1/2012 |
| JP | 2012-209763 A | 10/2012 |
| JP | 2014-532472 A | 12/2014 |

OTHER PUBLICATIONS

Office Action, dated Jul. 26, 2019, which issued during the prosecution of Chinese Patent Application No. 201580070108.0, which corresponds to the present application.

* cited by examiner

F I G . 1
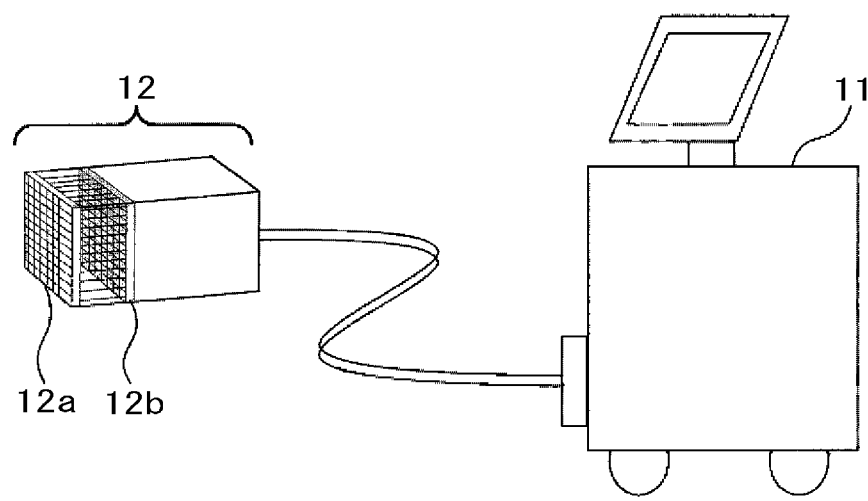

ULTRASONIC PROBE AND ULTRASONIC DIAGNOSIS DEVICE PROVIDED WITH SAME

CROSS REFERENCE TO PRIOR APPLICATIONS

This application is a U.S. National Phase application under 35 U.S.C. § 371 of International Application No. PCT/JP2015/083362, filed on Nov. 27, 2015, which claims benefit of priority to Japanese Application No. 2015-004624, filed on Jan. 14, 2015. The International Application was published in Japanese on Jul. 21, 2016 as WO 2016/114018 A1 under PCT Article 21(2). The contents of the above applications are hereby incorporated by reference.

TECHNICAL FIELD

The present invention relates to an ultrasonic probe and an ultrasonic diagnosis device provided with the same.

BACKGROUND ART

Ultrasonic diagnosis devices are widely used as devices capable of observing living organisms easily in real time together with X-ray computed tomography (CT) devices, magnetic resonance imaging (MRI) devices, and the like. Further, in recent years, their intended purpose has been expanded by utilization from conventional diagnostic imaging to treatment support such as puncture observation and contrast agent observation, and due to such a background, ultrasonic diagnosis devices are required to have a high image quality.

In the ultrasonic diagnosis devices, when there is a difference between a rising slew rate and a falling slew rate of a drive signal of an ultrasonic probe, a virtual image (artifact) occurs in a tomographic image or a blood flow image. For this reason, it is desirable that an adjustment can be performed so that the rising slew rate and the falling slew rate of the drive signal are equal to each other.

As an output circuit capable of adjusting the slew rate, Patent Document 1 discloses an electric waveform generating circuit which is capable of adjusting a slew rate, and includes a plurality of output circuits, an internal circuit that controls the output circuits, a replica gate having the same configuration as the output circuit, a slew rate adjustment pulse generation unit that controls an output timing of the replica gate, a switch unit that controls the slew rate of the replica gate, and an observation terminal that monitors an output signal of the replica gate, wherein an output waveform of the replica gate is monitored through the observation terminal, and the slew rate is adjusted to a desired slew rate through the switch unit.

CITATION LIST

Patent Document

Patent Document 1: JP 2001-119277 A

SUMMARY OF THE INVENTION

Problems to be Solved by the Invention

A dimension of the ultrasonic probe of the ultrasonic diagnosis device depends on various factors, and one of the factors is a size of a circuit that drives a transducer emitting ultrasonic waves or receives an electric signal emitted from the transducer. In order to improve usability of the ultrasonic probe, for example, so that an examiner can carry it easily and conveniently apply it to a body, the size of the circuit is required to be within a predetermined size. In the circuit disclosed in Patent Document 1, it is necessary to install a monitor device that observes the output signal of the replica gate and an operational device that calculates a control value for obtaining a desired slew rate from an observed waveform, and the circuit size is large, and thus a desired ultrasonic probe size is unable to be obtained although it is used for the ultrasonic probe.

In this regard, it is an object of the present invention to provide an ultrasonic probe capable of adjusting the slew rate while suppressing the dimension of the ultrasonic probe and the circuit size.

Solutions to Problems

The present application includes a plurality of means for solving the above problems, and as an example, an ultrasonic probe according to the present invention includes: a transducer; a transmitting circuit including a transducer driving unit and a current source, the transducer driving unit being configured with a current mirror of a low voltage transistor and a high voltage transistor, the high voltage transistor being connected to the transducer, the current source supplying an operating current to the low voltage transistor of the transducer driving unit; a correcting unit including a transmission circuit driving unit replica having the same configuration as the transducer driving unit, a bias unit that constantly maintains a sum of electric currents flowing to a low voltage transistor and a high voltage transistor of the transmitting circuit driving unit replica, and an observing unit that copies and extracts the electric current flowing to the low voltage transistor of the transmitting circuit driving unit replica; and a distributing unit that transfers a signal to a current source of the transmitting circuit so that the same current value as the current value extracted by the observing unit flows.

Effects of the Invention

According to the present invention, it is possible to provide an ultrasonic probe capable of adjusting the slew rate while suppressing the dimension of the ultrasonic probe and the circuit size.

Problems, configurations, and effects which are not described above will be apparent from description of embodiments to be described below.

BRIEF DESCRIPTION OF THE DRAWINGS

FIG. 1 is a diagram schematically illustrating an ultrasonic diagnosis device according to a first embodiment of the present invention.

MODE FOR CARRYING OUT THE INVENTION

Figure 2:
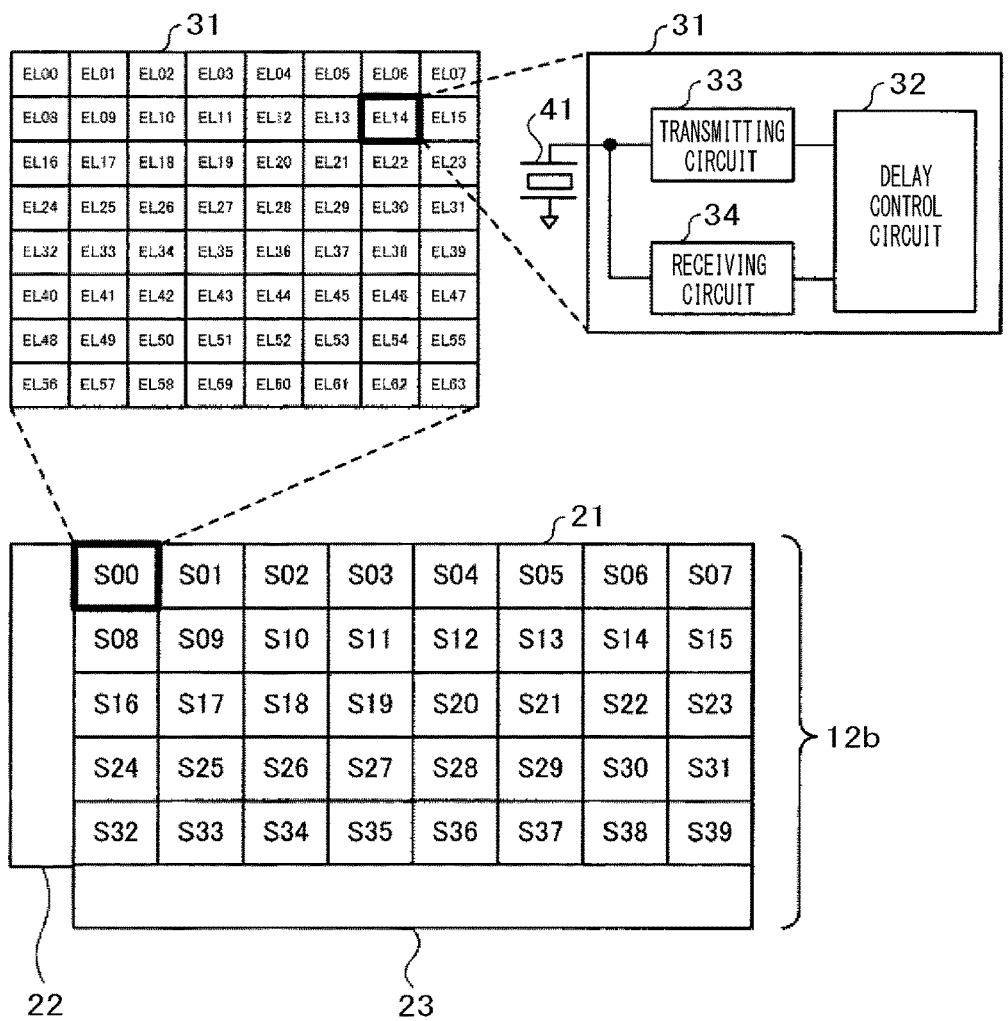
FIG. 2 is a diagram for describing a 2D array IC of an ultrasonic probe of FIG. 1.

Hereinafter, exemplary embodiments of the present invention will be described in detail below with reference to the appended drawings. In the drawings for describing embodiments, components having the same functions are given the same names and denoted by the same reference numerals, and repeated description thereof is omitted.

First Embodiment

FIG. 1 is a diagram illustrating an ultrasonic diagnosis device according to a first embodiment of the present invention. As illustrated in FIG. 1, the ultrasonic diagnosis device includes a device body 11 and an ultrasonic probe 12.

The device body 11 includes, for example, a central processor unit (CPU) that controls the ultrasonic diagnosis device in general, a storage device such as a hard disk drive (HDD) that stores programs executed by the CPU or a RAM that temporarily stores data to be processed, and a communication interface (IF) that performs communication with an external device. Further, the device body 11 includes, for example, various kinds of power supply circuits and an image processing circuit that performs image processing on signals output from the ultrasonic probe in the housing. For example, the device body 11 includes an input device such as a keyboard or a mouse and an output device such as a liquid crystal display device. For example, the input device may be a touch panel installed in a liquid crystal display device. The device body 11 has a structure that is freely movable on a floor surface by a castor or the like attached to a bottom surface thereof.

The ultrasonic probe 12 has a two-dimensional (2D) array transducer 12a and a 2D array integrated circuit (IC) 12b. The 2D array transducer 12a includes a plurality of transducers each of which emit an ultrasonic wave on the side of the ultrasonic probe 12 that comes into contact with a human body. Pluralities of transducers of the 2D array transducer 12a are arranged two dimensionally (in a planar form).

The 2D array IC 12b includes a plurality of circuits that face the 2D array transducer 12a and drive the transducers of the 2D array transducer 12a. Pluralities of circuits of the 2D array IC 12b are arranged in two dimensionally.

Pluralities of circuits of the 2D array IC 12b are installed corresponding to a plurality of transducers of the 2D array transducer 12a. For example, one circuit of the 2D array IC 12b is electrically connected to one transducer of the 2D array transducer 12a.

FIG. 2 is a diagram for describing the 2D array IC of FIG. 1. The 2D array IC 12b illustrated in FIG. 1 is illustrated in FIG. 2. As illustrated in a lower part of FIG. 2, the 2D array IC 12b includes a plurality of sub arrays 21 and peripheral circuits 22 and 23.

For example, the sub arrays 21 and the peripheral circuits 22 and 23 are formed on one IC chip. In FIG. 2, 40 sub arrays 21 (S00 to S39) are formed on the IC. Further, in FIG. 2, two peripheral circuits 22 and 23 are formed on the IC.

Although not illustrated, each of the peripheral circuits 22 and 23 has an IF circuit that performs communication with the device body 11. Although not illustrated, each of the peripheral circuits 22 and 23 has a control circuit that controls a plurality of sub arrays 21 on the basis of an instruction given from the device body 11.

As illustrated on an upper left side of FIG. 2, each of a plurality of sub arrays 21 includes a plurality of element circuits 31. In FIG. 2, an example of the element circuits 31 of the sub array 21 of "S00" is illustrated. One sub array 21 includes 64 element circuits 31 (EL00 to EL63).

Pluralities of transducers of the 2D array transducer 12a are downsized in accordance with demands for high image quality, and the number thereof is increased. Accordingly, the number of element circuits 31 reaches, for example, about 10,000. Therefore, reduction in size and power consumption of the element circuit 31 is important. In FIG. 2, for the sake of simplification of illustration, an example of 40 (S00 to S39)×64 (EL00 to EL63) element circuit 31 is illustrated.

As illustrated on the upper right side of FIG. 2, each of a plurality of element circuits 31 includes a delay control circuit 32, a transmitting circuit 33, and a receiving circuit 34. FIG. 2 illustrates a circuit block example of the element circuit 31 of "EL 14." FIG. 2 also illustrates a transducer 41 of the 2D array transducer 12a which is connected to the element circuit 31.

The element circuits 31 (for example, EL00 to EL07 or the like) in the same row are connected to a common low voltage power supply circuit and a common high voltage power supply circuit (not illustrated) included in the peripheral circuits 22 and 23. For example, the element circuits 31 in the same row are connected to a pair of positive and negative low voltage power supply wirings. Further, the element circuits 31 in the same row are connected to a pair of positive and negative high voltage power supply wirings. Hereinafter, the positive low voltage power supply wiring is also referred to as a power source VDD, and a negative low voltage power supply wiring is also referred to as a power source VSS. Further, the high-voltage positive power supply is also referred to as a power source HVDD, and the high-voltage negative power supply wiring is also referred to as a power source HVSS.

In accordance with the control from the device body 11, the delay control circuit 32 controls an output timing of a drive signal which is output from the transmitting circuit 33 and used for driving the transducer 41. For example, the delay control circuit 32 controls the output timing of the drive signal outputted from the transmitting circuit 33 such that focus points of a plurality of ultrasonic waves (points at which the ultrasonic waves overlap) output from a plurality of transducers of the 2D array transducer 12a are scanned. For example, the delay control circuit 32 controls a reception timing of the receiving circuit 34 such that an appropriate image of a target is obtained from a plurality of reflected waves received by a plurality of transducers of the 2D array transducer 12a. The delay control circuit 32 transmits the signal of the reflected wave received by the receiving circuit 34 to the device body 11. As a result, the device body 11 can perform image processing on the signal received from the delay control circuit 32 and cause the image of the target to be displayed on the output device.

The transmitting circuit 33 outputs the drive signal for driving the transducer 41 on the basis of the signal output from the delay control circuit 32. The transmitting circuit 33 can vary the amplitude of the drive signal to be output to the transducer 41. Further, the transmitting circuit 33 can adjust the slew rate of the drive signal to be output to the transducer 41.

The receiving circuit 34 amplifies the signal received by the transducer 41 and outputs the amplified signal to the delay control circuit 32.

Figure 3:
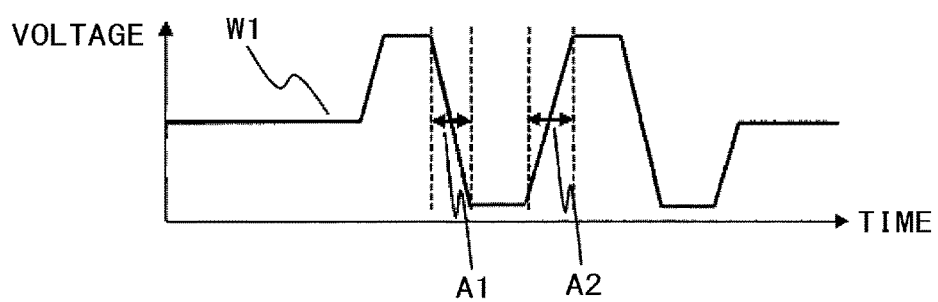
FIG. 3 is a diagram for describing slew rate compensation of a transmitting circuit.

FIG. 3 is a diagram for describing slew rate compensation of the transmitting circuit of FIG. 2. FIG. 3 illustrates a waveform W1 of the drive signal output from the transmitting circuit 33 to the transducer 41.

When there is a difference between the rising slew rate and the falling slew rate of the drive signal, a virtual image (artifact) occurs in a tomographic image or a blood flow image. For this reason, the transmitting circuit 33 is configured to be able to perform an adjustment so that the rising slew rate and the falling slew rate of the drive signal are equal to each other. For example, the transmitting circuit 33 is configured to be able to adjust the falling slew rate of the drive signal indicated by an arrow A1 in FIG. 3 and the rising slew rate of the drive signal indicated by an arrow A2. The virtual image (artifact) can be reduced by adjusting the rising slew rate and the falling slew rate and performing compensation so that the difference is reduced.

Figure 4:
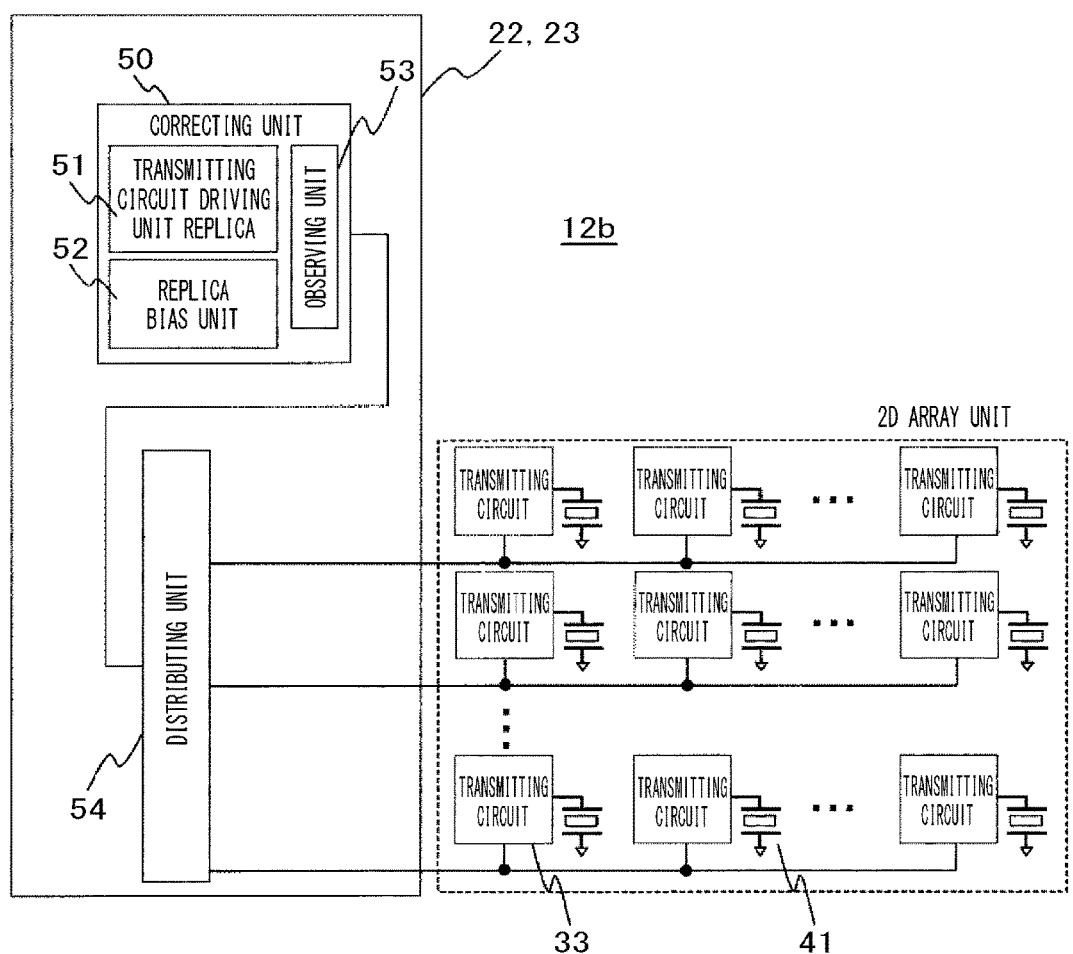
FIG. 4 is a diagram illustrating a block configuration example of a transmitting circuit and a slew rate compensating circuit according to the first embodiment of the present invention.

FIG. 4 is a diagram illustrating a block configuration example of the transmitting circuit and the slew rate compensating circuit of FIG. 2.

As illustrated in FIG. 4, the correcting unit 50 includes a transmitting circuit driving unit replica 51, a replica bias unit 52, and an observing unit 53. The correcting unit 50 is arranged in each of the peripheral circuits 22 and 23, and for example, only one circuit is installed on the 2D array IC, and the drive current of the transmitting circuit 33 having the compensated slew rate which is generated by the correcting unit 50 is distributed by a distributing unit 54 and transmitted to the respective transmitting circuits 33. For example, the distributing unit 54 is disposed in each of the peripheral circuits 22 and 23, and performs transmission to the transmitting circuits 33 via electric wirings in a row or column direction. FIG. 4 illustrates transmission through the electric wirings in the row direction.

Although not illustrated, the correcting unit 50 outputs two slew rate compensation drive currents, that is, a rising compensation drive current and a falling compensation drive current, and the distributing unit 54 also transmits the rising compensation drive current and the falling compensation drive current to the transmitting circuit 33. In order to reduce power consumption, the distributing unit 54 converts an input compensation drive current into a voltage and transmits a voltage signal to each of the transmitting circuits 33 as a compensation drive signal.

Figure 5:
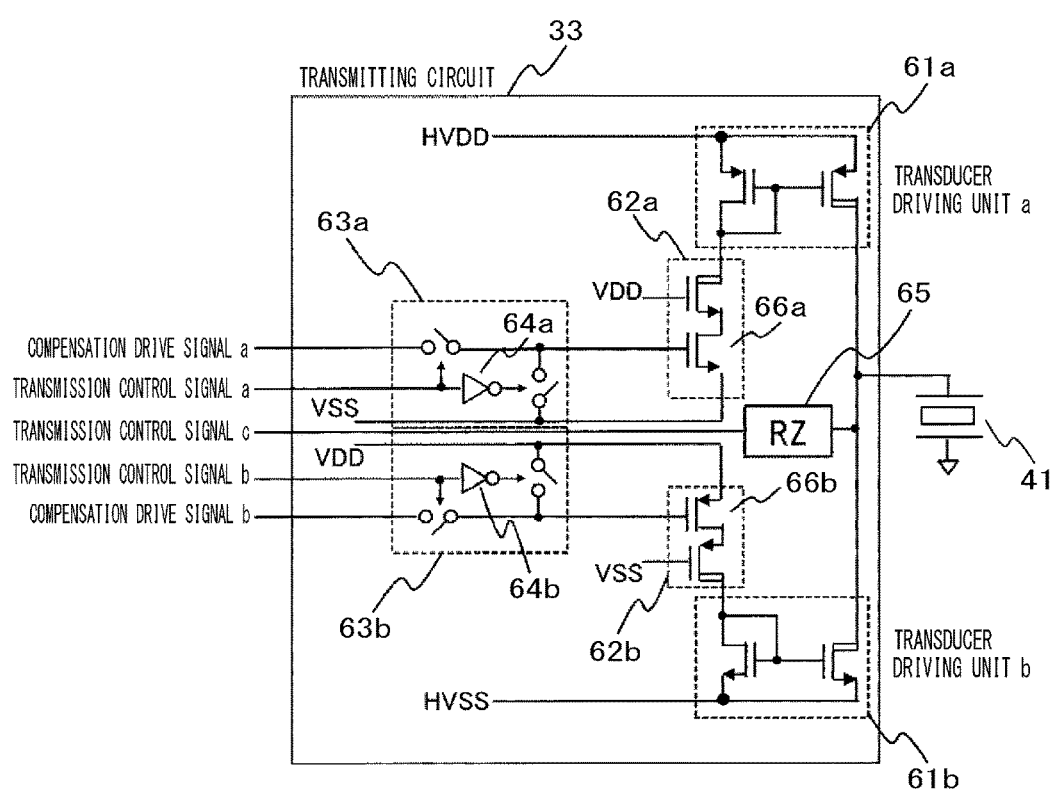
FIG. 5 is a diagram illustrating an example of the transmitting circuit of FIG. 4.

FIG. 5 is a diagram illustrating an example of a circuit of the wave transmitting unit of FIG. 4.

As illustrated in FIG. 5, the transmitting circuit 33 includes a transducer driving unit a (61a) that applies HVDD which is a positive high voltage to the transducer 41, a high withstand voltage current source 62a that generates a drive current of the transducer driving unit a, and a transmission control circuit 63a that performs ON/OFF control on the high withstand voltage current source 62a, and when a transmission control signal a is enabled, a compensation drive signal a is applied to a transistor 66a of the high withstand voltage current source 62a, the transistor 66a allows an electric current related to a value of the compensation drive signal a to flow to the transducer driving unit a (61a), and the transducer driving unit a (61a) allows an electric current of a value related to the electric current of the high withstand voltage current source 62a to flow the transducer 41. The transistor on the left side of the transducer driving unit a is a low voltage transistor, the transistor connected to the transducer 41 on the right side is a high voltage transistor, and a current mirror configuration is constituted by the low voltage transistor and the high voltage transistor.

Further, the transmitting circuit 33 includes a transducer driving unit b (61b) that applies HVSS which is a negative high voltage to the transducer 41, a high withstand voltage current source 62b that generates a drive current of the transducer driving unit b, and a transmission control circuit 63b that performs ON/OFF control on the transmission control signal b, and when a transmission control signal b is enabled, a compensation drive signal b is applied to a transistor 66b of the high withstand voltage current source 62b, the transistor 66b allows an electric current related to a value of the compensation drive signal b to the transducer driving unit b (61b), and the transducer driving unit b extracts an electric current of a value related to the electric current of the high withstand voltage current source 62b from the transducer 41. The transistor on the left side of the transducer driving unit b (61b) is a low voltage transistor, the transistor connected to the transducer 41 on the right side is a high voltage transistor, and a current mirror configuration is constituted by the low voltage transistor and the high voltage transistor.

Further, the transmitting circuit 33 includes an RZ circuit 65, and when a transmission control signal c is enabled, a potential of GND is applied to the transducer 41.

Figure 6:
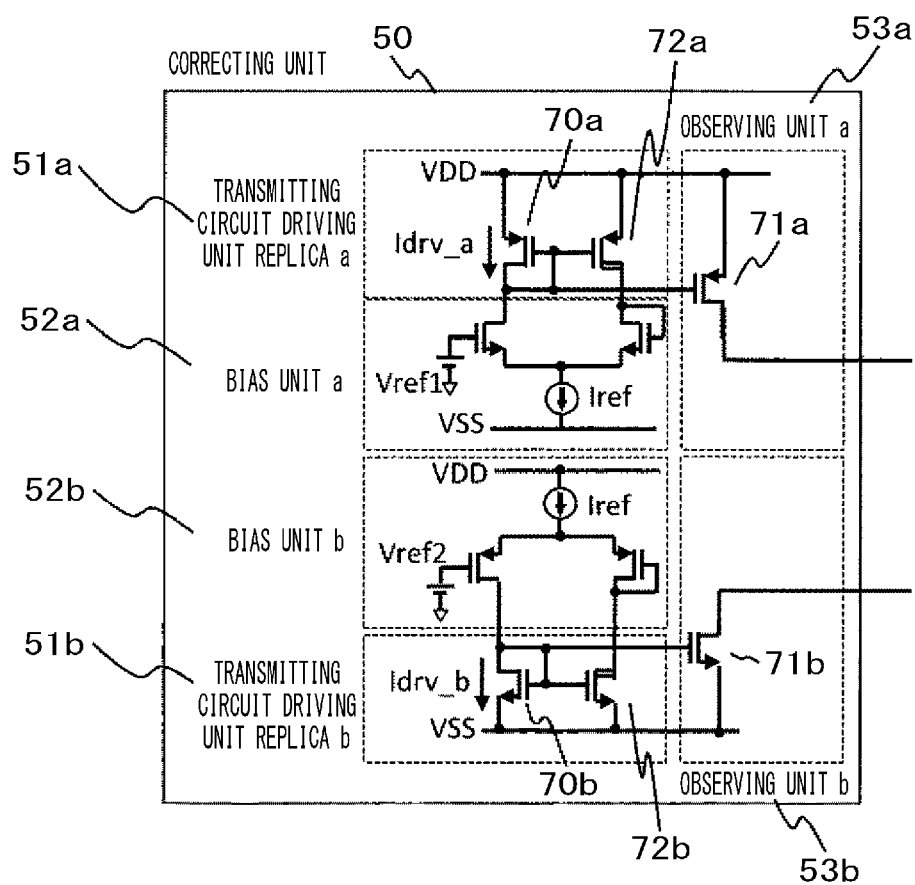
FIG. 6 is a diagram illustrating a circuit example of a correcting unit of FIG. 4.

FIG. 6 is a diagram illustrating a circuit example of the correcting unit of FIG. 4.

As illustrated in FIG. 6, the correcting unit 50 includes a transmitting circuit driving unit replica a (51a) that generates a drive current for compensating the rising slew rate, a bias unit a (52a) that supplies the driving current to the transmitting circuit driving unit replica a, and an observing unit a (53a) that copies and extracts the compensation drive current a obtained by the transmitting circuit driving unit replica a. The transmitting circuit driving unit replica a (51a) has the same configuration as the transducer driving unit a (61a).

Here, a ratio of an electric current flowing through the low voltage transistor 70a and an electric current flowing through a high voltage transistor 72a is set to 1:M (a current mirror ratio). The transmission circuit driving unit replica a (51a) has the configuration of the current mirror, but since the configuration of the current mirror is constituted by the low voltage transistor and the high voltage transistor, the current mirror ratio (1:M) varies due to a manufacturing variation occurring when an IC is manufactured or the temperature during operation of an IC. A current mirror ratio obtained by considering a variation rate E is 1:E×M. Therefore, when the electric current of the low voltage transistor 70a is indicated by Idrv_a, the electric current flowing through the high voltage transistor 72a is indicated by Formula 1.

[Math. 1]

$$Idrv\_a\_h = E*M*Idrv\_a \quad \text{(Formula 1)}$$

Meanwhile, a sum of the electric current flowing through the low voltage transistor 70a and the electric current flowing through the high voltage transistor 72a at a reference current source of the bias unit a (52a) is a constant value (Iref).

[Math. 2]

$$Iref = Idrv\_a + Idrv\_a\_h \quad \text{(Formula 2)}$$

From Equation 1 and Equation 2, Idrv_a is indicated by Formula (3).

[Math. 3]

$$Idrv\_a = \frac{Iref}{(1+E*M)} \cong \frac{Iref}{E*M} (\because E*M \gg 1) \quad \text{(Formula 3)}$$

A transistor 71a of the observing unit a (53a) is a transistor having the same size as the low voltage transistor 70a and has a current mirror configuration. Therefore, Idrv_a can be copied by the observing unit a (53a). Copied Idrv_a is transferred to the distributing unit 54, converted into the compensation driving signal a, and transmitted to the high withstand voltage current source 62a of each transmitting circuit. The high withstand voltage current source 62a converts the compensation drive signal a into the electric current Idrv_a and applies the electric current Idrv_a to the low voltage transistor of transducer driving unit a (61a). Since the transducer driving unit a (61a) and the transmitting circuit driving unit replica a (51a) have the same configuration, when Idrv_a is applied to the low voltage transistor, an electric current Iout_a flowing through the high voltage transistor is obtained as in Formula 4.

[Math. 4]

$$Iout\_a = E*M*\frac{Iref}{E*M} = Iref \quad \text{(Formula 4)}$$

The reference current Iref that is constant independent of the variation rate E flows. Further, since the transducer 41 can be equivalently regarded as a parallel circuit of a capacitor and a resistor, the slew rate is decided by an electric current that flows in. Accordingly, it is possible to compensate the rising slew rate for a variation caused by a manufacturing variation occurring when an IC is manufactured or the temperature during operation of an IC.

Further, the correcting unit 50 includes a transmitting circuit driving unit replica b (51b) that generates a drive current for compensating the falling slew rate, a bias unit b (53b) that supplies the driving current to the transmitting circuit driving unit replica b, and an observing unit b (53b) that copies and extracts the compensation drive current b obtained by the transmitting circuit driving unit replica b (51b). The transmitting circuit driving unit replica b (51b) has the same configuration as the transducer driving unit b (61b).

Here, a ratio of an electric current flowing to the low voltage transistor 70b and an electric current flowing to the high voltage transistor 72b is 1:M (the current mirror ratio). Similarly to the above example, the transmitting circuit driving unit replica b (51b) has the configuration of the current mirror, but since the configuration of the current mirror is constituted by the low voltage transistor and the high voltage transistor, the current mirror ratio (1:M) varies due to a manufacturing variation occurring when an IC is manufactured or the temperature during operation of an IC. A current mirror ratio obtained by considering a variation rate E is 1:E×M. Therefore, when the electric current of the low voltage transistor 70b is indicated by Idrv_b, the electric current flowing through the high voltage transistor 72b is indicated by Formula 5.

[Math. 5]

$$Idrv\_b\_h = E*M*Idrv\_b \quad \text{(Formula 5)}$$

Meanwhile, a sum of the electric current flowing through the low voltage transistor 70b and the electric current flowing through the high voltage transistor 72b at a reference current source of the bias unit b (52b) is a constant value (Iref).

[Math. 6]

$$Iref = Idrv\_b + Idrv\_b\_h \quad \text{(Formula 6)}$$

From Equations 5 and 6, Idrv_b is indicated by Formula (7).

[Math. 7]

$$Idrv\_b = \frac{Iref}{(1+E*M)} \cong \frac{Iref}{E*M} (\because E*M \gg 1) \quad \text{(Formula 7)}$$

A transistor 71b of the observing unit b (53b) is a transistor having the same size as the low voltage transistor 70b and takes a current mirror configuration. Therefore, Idrv_b can be copied by the observing unit b (53b). Copied Idrv_b is transferred to the distributing unit 54, converted into the compensation driving signal b, and transmitted to the high withstand voltage current source 62b of each transmitting circuit. The high withstand voltage current source 62b converts the compensation drive signal b into the electric current Idrv_b and applies the electric current Idrv_b to the low voltage transistor of transducer driving unit b (61b). Since the transducer driving unit b (61b) and the transmitting circuit driving unit replica a (51b) have the same configuration, when Idrv_b is applied to the low voltage transistor, an electric current Iout_b flowing through the high voltage transistor is obtained as in Formula 8.

[Math. 8]

$$Iout\_b = E*M*\frac{Iref}{E*M} = Iref \quad \text{(Formula 8)}$$

The reference current Iref that is constant independent of the variation rate E flows. Further, as described above, since the transducer 41 can be equivalently regarded as a parallel circuit of a capacitor and a resistor, the slew rate is decided by an electric current that flows in. Accordingly, it is possible to compensate the rising slew rate for a variation caused by a manufacturing variation occurring when an IC is manufactured or the temperature during operation of an IC.

Figure 7:
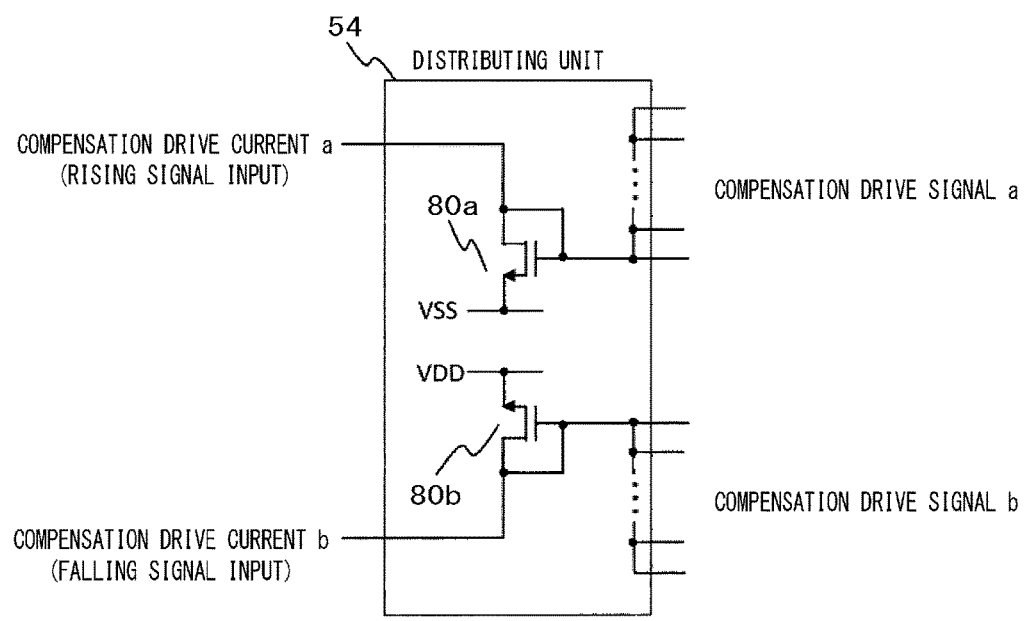
FIG. 7 is a diagram illustrating a circuit example of a distributing unit of FIG. 4.

FIG. 7 is a diagram illustrating a circuit example of the distributing unit of FIG. 4.

As illustrated in FIG. 7, the distributing unit 54 includes a low voltage transistor 80a that converts the compensation drive current a for compensating for the rising slew rate which is input from the correcting unit 50 into the compensation drive signal a and a low voltage transistor 80b that converts the compensation drive current b for compensating the falling slew rate into the compensation drive signal b.

A gate voltage generated by short-circuiting the drain and the gate of the low voltage transistor 80a and causing the compensation drive current a to flow into the drain is transmitted to each transmitting circuit as the compensation drive signal a. Here, the low voltage transistor 80*a* and the transistor 66*a* of the high withstand voltage current source of the transmitting circuit have the same transistor size and have a current mirror configuration. Accordingly, the same electric current as the compensation drive current a input to the low voltage transistor 80*a* can flow to the transistor 66*a*.

Further, a gate voltage generated by short-circuiting the drain and the gate of the low voltage transistor 80*b* and extracting the compensation drive current b from the drain is transmitted to each transmitting circuit as the compensation drive signal b. Here, the low voltage transistor 80*b* and the transistor 66*b* of the high withstand voltage current source of the transmitting circuit have the same transistor size and have the current mirror configuration. Accordingly, the same electric current as the compensation drive current b input to the low voltage transistor 80*b* can flow to the transistor 66*b*.

Figure 8:
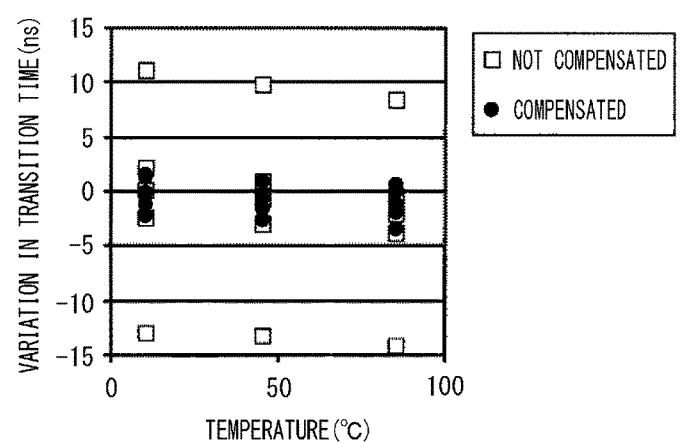
FIG. 8 is a diagram illustrating a simulation result of slew rate compensation of FIG. 4.

FIG. 8 is a diagram illustrating a simulation result of the slew rate compensation of FIG. 4.

FIG. 8 illustrates a difference between a rising transition time and a falling transition time of the drive signal at a total of 15 points, that is, three points of operation temperature of an IC and five points of each of semiconductor process variations (typical, fast-fast, slow-slow, fast-slow, and slow-fast). A standard deviation when compensation of the present invention is performed is 0.9 ns and 5.24 ns when compensation of the present invention is not performed, and thus the standard deviation can be reduced to about ⅕.

According to the present embodiment, the slew rate can be adjusted while suppressing the dimension and the circuit size of the ultrasonic probe.

Second Embodiment

It is desirable that the slew rate of the drive signal of the transducer can be controllable from the device. It is because since the quality of the ultrasonic tomographic image is affected by factors such as a transducer characteristic and an ultrasonic signal phasing method, it is necessary to set a desired slew rate according to such characteristics. The second embodiment will be described focusing on a circuit that compensates the rising slew rate and the falling slew rate from the set desired slew rate.

Figure 9:
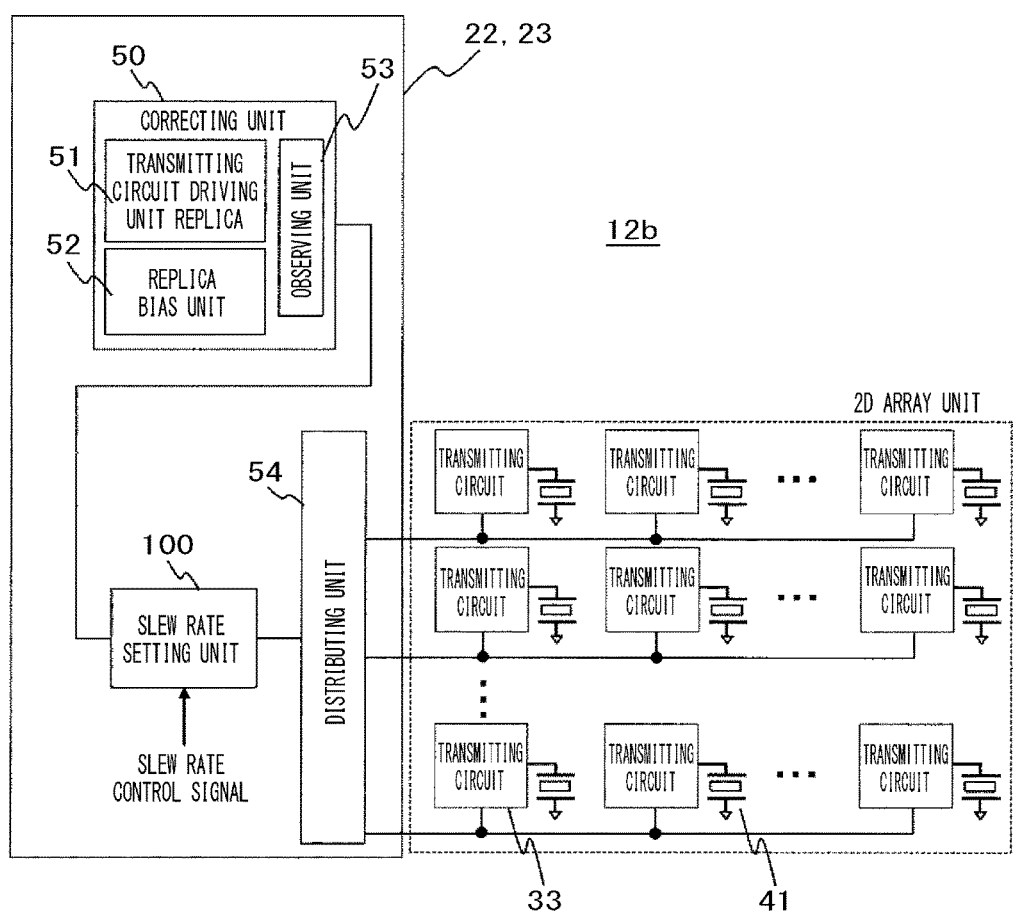
FIG. 9 is a diagram illustrating a block configuration example of a transmitting circuit and a slew rate compensating circuit according to a second embodiment of the present invention.

FIG. 9 is a diagram illustrating a block example of a transmitting circuit and a slew rate compensating circuit according to the second embodiment.

As illustrated in FIG. 9, each of the peripheral circuits 22 and 23 has a slew rate setting unit 100. The slew rate setting unit 100 receives an output signal of the correcting unit 50. The output of slew rate setting unit 100 is connected to an input of distributing unit 54.

Figure 10:
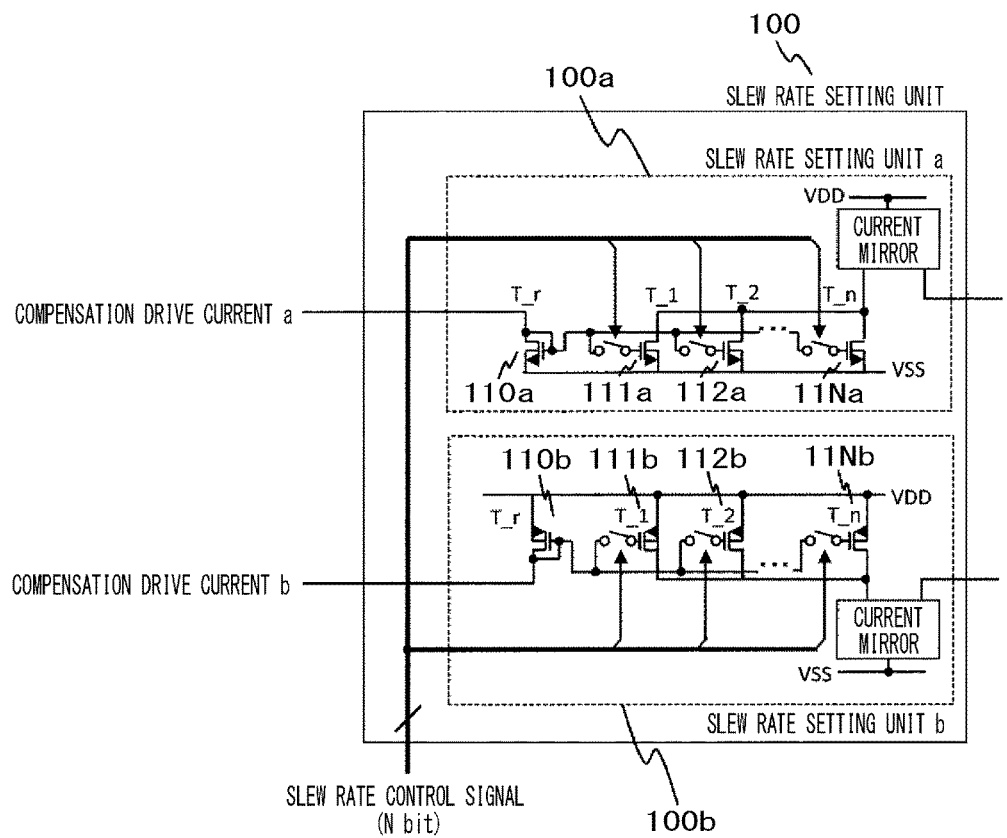
FIG. 10 is a diagram illustrating a circuit example of a slew rate setting unit of FIG. 9.

FIG. 10 is a diagram illustrating a circuit example of the slew rate setting unit according to the second embodiment.

As illustrated in FIG. 10, the slew rate setting unit 100 includes a slew rate setting unit a (100*a*) that sets the rising slew rate and a slew rate setting unit b (100*b*) that sets the falling slew rate.

The slew rate setting unit a (100*a*) receives the compensation drive current a output from the correcting unit 50. The output of the slew rate setting unit a (100*a*) is connected to a rising signal input of the distributing unit 54 illustrated in FIG. 7. The slew rate setting unit a (100*a*) includes a transistor group 110*a* and N transistor groups 111*a* to 11N*a* which are configured such that transistors having the same size are connected in parallel. In FIG. 10, only the transistor groups 110*a*, 111*a*, 112*a*, and 11N*a* are illustrated. The drain and the gate of the transistor group 110*a* are connected, and the compensation drive current a flows into the drain. The transistor group 110*a* and one transistor constituting the transistor group of 111*a* to 11N*a* have the same size. A gate of the transistor group 110*a* and a gate of the transistor groups 111*a* to 11N*a* are connected through a switch. The switch is turned on or off in accordance with an N-bit slew rate control signal. For example, if the number of transistors constituting the transistor group 110*a* is indicated by T_r, and the number of transistors constituting the transistor group constituting the transistor group 111*a* is indicated by T_1, when the switch between the transistor group 110*a* and the transistor group 111*a* is turned on, the two transistor groups constitute a current mirror having a ratio of T_r:T_1. Further, when the switch between the transistor group 110*a* and the transistor groups 111*a* and 112*a* is turned on, a current mirror having a ratio of T_r:(T_1+T_2) is constituted. In other words, the slew rate setting unit a (100*a*) is a current mirror capable of controlling the ratio in accordance with the slew rate control signal. An electric current Icnt_a output from the slew rate setting unit a (100*a*) is indicated by Formula 9.

[Math. 9]

$$\mathrm{Icnt\_a} = \frac{T\_t}{T\_r} * \mathrm{Idrv\_a} = \frac{T\_t}{T\_r} * \frac{Iref}{E*M} \qquad \text{(Formula 9)}$$

Here, T_t indicates a total of the number of transistors constituting the transistor group whose switch is on among the transistor groups 111*a* to 11N*a*.

The output current Icnt_a of this slew rate setting unit a (100*a*) is transmitted to each transmission circuit 33 through the distributing unit 54. Therefore, the electric current Iout_a flowing to the high voltage transistor of the transducer driving unit a (61*a*) of the transmitting circuit 33 is obtained as in Formula 10.

[Math. 10]

$$\mathrm{Iout\_a} = \mathrm{Icnt\_a} * E * M = \frac{T\_t}{T\_r} * Iref \qquad \text{(Formula 10)}$$

In other words, the electric current Iout_a has a value obtained by multiplying the reference current Iref by (T_t/T_r).

Further, since the transducer 41 can be equivalently regarded as a parallel circuit of a capacitor and a resistor, the slew rate is decided by an electric current that flows in. In other words, it is possible to adjust Iout_a and change the rising slew rate by controlling the value of T_t in accordance with the slew rate control signal.

Further, the compensation drive current b output from correcting unit 50 is input to the slew rate setting unit b (100*b*). An output of the slew rate setting unit b (100*b*) is connected to a falling signal input of the distributing unit 54 illustrated in FIG. 7. The slew rate setting unit b (100*b*) includes a transistor group 110*b* and N transistor groups 111*b* to 11N*b* which are configured such that transistors having the same size are connected in parallel. In FIG. 10, only the transistor groups 110*b*, 111*b*, 112*b*, and 11N*b* are illustrated. The drain and the gate of the transistor group 110*b* are connected, and the compensation drive current b flows into the drain. The transistor group 110b and one transistor constituting the transistor group of 111b to 11Nb have the same size. A gate of the transistor group 110b and a gate of the transistor groups 111b to 11Nb are connected through a switch. The switch is turned on or off in accordance with an N-bit slew rate control signal. For example, if the number of transistors constituting the transistor group 110b is indicated by T_r, and the number of transistors constituting the transistor group constituting the transistor group 111b is indicated by T_1, when the switch between the transistor group 110b and the transistor group 111b is turned on, the two transistor groups constitute a current mirror having a ratio of T_r:T_1. Further, when the switch between the transistor group 110b and the transistor groups 111b and 112b is turned on, a current mirror having a ratio of T_r:(T_1+T_2) is constituted. In other words, the slew rate setting unit b (100b) is a current mirror capable of controlling the ratio in accordance with the slew rate control signal. An electric current Icnt_b output from the slew rate setting unit b (100b) is indicated by Formula 11.

[Math. 11]

$$\text{Icnt\_b} = \frac{T\_t}{T\_r} * \text{Idrv\_b} = \frac{T\_t}{T\_r} * \frac{Iref}{E*M} \quad \text{(Formula 11)}$$

Here, T_t indicates a total of the number of transistors constituting the transistor group whose switch is on among the transistor groups 111b to 11Nb.

The output current Icnt_b of this slew rate setting unit b (100b) is transmitted to each transmission circuit 33 through the distributing unit 54. Therefore, the electric current Iout_b flowing to the high voltage transistor of the transducer driving unit b (61b) of the transmitting circuit 33 is obtained as in Formula 12.

[Math. 12]

$$\text{Iout\_b} = \text{Icnt\_b} * E * M = \frac{T\_t}{T\_r} * Iref \quad \text{(Formula 12)}$$

In other words, the electric current Iout_a has a value obtained by multiplying the reference current Iref by (T_t/T_r).

Further, since the transducer 41 can be equivalently regarded as a parallel circuit of a capacitor and a resistor, the slew rate is decided by an electric current that is extracted. In other words, it is possible to adjust Iout_b and change the falling slew rate by controlling the value of T_t in accordance with the slew rate control signal.

According to the present embodiment, it is possible to change the rising slew rate and the falling slew rate on the basis of the slew rate control signal.

Third Embodiment

It is desirable that a difference between the rising slew rate and the falling slew rate be small. A third embodiment will be described focusing on a circuit that performs the slew rate compensation with a high degree of accuracy.

Figure 11:
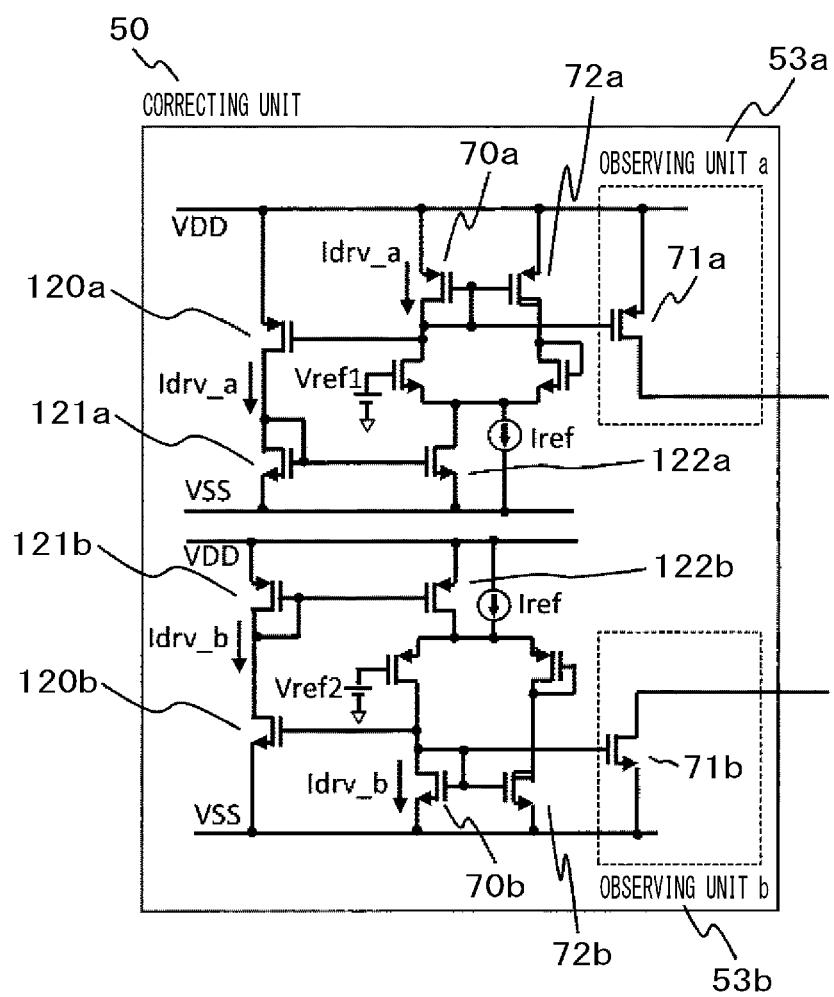
FIG. 11 is a diagram illustrating a circuit example of a correcting unit according to a third embodiment of the present invention.

FIG. 11 is a diagram illustrating a circuit example of a correcting unit according to the third embodiment.

As illustrated in FIG. 11, the correcting unit 50 according to the third embodiment includes transistors 120a, 121a, 122a, 120b, 121b, and 122b.

The transistor 120a has the same size as the transistor 70a, and the transistor 120a and the transistor 70a constitute a one-to-one current mirror. In other words, the drain electric current of Idrv_a flows to the transistor 120a. A drain and a gate of the transistor 121a are connected, and the drain electric current of the transistor 120a flows into the drain. Further, the transistor 122a has the same size as the transistor 121a, and the transistor 121a and the transistor 122a constitute a one-to-one current mirror. Therefore, the electric current of Idrv_a flows to the transistor 122a. If an electric current flowing to the high voltage transistor 72a is indicated by E*M*Idrv_a (M is a magnification of the transistor 70a and the high voltage transistor 72a, and E is the variation rate),

[Math. 13]

$$Idrv\_a + Iref = Idrv\_a + E*M*Idrv\_a \quad \text{(Formula 13)}$$

Formula 13 is held.

[Math. 14]

$$Idrv\_a = \frac{Iref}{E*M} \quad \text{(Formula 14)}$$

Accordingly, Formula 14 is held. In Formula 3 of the first embodiment, an error occurs with an approximation of E*M≫1, but no error of an approximation occurs in Formula 13. In other words, the correction accuracy of the rising slew rate can be improved.

Further, the transistor 120b has the same size as the transistor 70b, and the transistor 120b and the transistor 70b constitute a one-to-one current mirror. In other words, the drain electric current of Idrv_b flows to the transistor 120b. A drain and a gate of the transistor 121b are connected, and the drain electric current of the transistor 120b is extracted to the drain. Further, the transistor 122b has the same size as the transistor 121b, and the transistor 121b and the transistor 122b constitute a one-to-one current mirror. Therefore, the electric current of Idrv_b flows to the transistor 122b. If an electric current flowing to the high voltage transistor 72b is indicated by E*M*Idrv_b (M is a magnification of the transistor 70b and the high voltage transistor 72b, and E is the variation rate),

[Math. 15]

$$Idrv\_b + Iref = Idrv\_b + E*M*Idrv\_b \quad \text{(Formula 15)}$$

Formula 15 is held.

[Math. 16]

$$Idrv\_b = \frac{Iref}{E*M} \quad \text{(Formula 16)}$$

Accordingly, Formula 16 is held. In Formula 7 of the first embodiment, an error occurs with an approximation of E*M≫1, but no error of an approximation occurs in Formula 16. In other words, the correction accuracy of the falling slew rate can be improved.

According to the present embodiment, the slew rate compensation can be performed with a high degree of accuracy.

The present invention is not limited to the above embodiments and includes various modified examples. For example, in the above embodiments, the entire system has been described in detail in order to help with understanding of the present invention, and the present invention is not necessarily limited to those having all the components described above. Further, some components of an embodiment may be replaced with components of another embodiment, and components of another embodiment may be added to components of an embodiment. Furthermore, addition, deletion, and substitution of other components may be performed on some components of each embodiment. Moreover, the components, the functions, the processing units, or the processes described above may be implemented by hardware, for example, by designing some or all of them by an integrated circuit (IC).

REFERENCE SIGNS LIST 11 device body
12 ultrasonic probe
12a 2D array transducer
12b 2D array IC
21 sub array
22, 23 peripheral circuit
31 element circuit
32 delay control circuit
33 transmitting circuit
34 receiving circuit
41 transducer
50 correcting unit
51 transmitting circuit driving unit replica
52 replica bias unit
53 observing unit
54 distributing unit
61a transducer driving unit a
61b transducer driving unit b
62a high withstand voltage current source a
62b high withstand voltage current source b
63a transmission control circuit a
63b transmission control circuit b
62 RZ circuit
100 slew rate setting unit

The invention claimed is:

1. An ultrasonic probe, comprising:
an ultrasonic transducer;
a transmitting circuit including a transducer driving unit and a current source, the transducer driving unit being configured with a current mirror of a first voltage transistor and a second voltage transistor, the second voltage transistor being connected to the ultrasonic transducer, the current source supplying an operating current to the first voltage transistor of the transducer driving unit;
a correcting unit including a transmission circuit driving unit replica having the same configuration as the transducer driving unit, a bias unit that constantly maintains a sum of electric currents flowing to a third voltage transistor and a fourth voltage transistor of the transmitting circuit driving unit replica, and an observing unit that copies and extracts the electric current flowing to the third voltage transistor of the transmitting circuit driving unit replica; and
a distributing unit operatively connected with the transmitting circuit with electric wiring.

2. The ultrasonic probe according to claim 1, wherein the transmitting circuit and the correcting unit are formed on a same IC chip.

3. The ultrasonic probe according to claim 1,
wherein the observing unit includes a fifth voltage transistor, and
the current mirror is constituted by the fifth voltage transistor of the observing unit and the third voltage transistor of the transmitting circuit driving unit replica.

4. The ultrasonic probe according to claim 1,
wherein each of the distributing unit and the current source of the transmitting circuit includes a transistor, and
an output current of the observing unit is applied to a drain of the transistor of the distributing unit, and a current mirror is constituted by the transistor of the distributing unit and the transistor of the current source of the transmitting circuit.

5. The ultrasonic probe according to claim 1, wherein the bias unit includes a seventh voltage transistor connected to the third voltage transistor of the transmitting circuit driving unit replica, an eighth voltage transistor connected to the fourth voltage transistor of the transmitting circuit driving unit replica, and a reference current source, and a bias voltage is applied to a gate of the seventh voltage transistor, a gate of the eighth voltage transistor is connected to a drain of the eighth voltage transistor, and a differential pair is constituted by the seventh voltage transistor, the eighth voltage transistor, and the reference current source.

6. The ultrasonic probe according to claim 5, further comprising: a ninth voltage transistor that constitutes the current mirror with the third voltage transistor of the transmitting circuit driving unit replica; a tenth voltage transistor including a drain to which an electric current output from the ninth voltage transistor is applied and the drain and a gate of the tenth voltage transistor are connected; and a eleventh voltage transistor that constitutes the current mirror with the tenth voltage transistor and includes a drain which is connected to the seventh voltage transistor and the eighth voltage transistor.

7. The ultrasonic probe according to claim 1,
wherein an output of the distributing unit is connected to a plurality of transmitting circuits.

8. The ultrasonic probe according to claim 1, further comprising, a slew rate setting unit between the correcting unit and the distributing unit, the slew rate setting unit setting a slew rate of a drive signal of the ultrasonic transducer on a basis of a slew rate setting signal.

9. The ultrasonic probe according to claim 8,
wherein the slew rate setting unit includes a variable current source, wherein an input of the variable current source is connected to an output of the observing unit, and an output of the variable current source is connected to the distributing unit.

10. An ultrasonic diagnostic device, comprising:
the ultrasonic probe according to claim 1.

* * * * *